United States Patent
Sulur et al.

(10) Patent No.: US 9,066,861 B2
(45) Date of Patent: *Jun. 30, 2015

(54) DERMACEUTICAL CREAM MADE USING SODIUM FUSIDATE AND STEROIDS

(76) Inventors: Vanangamudi Subramaniam Sulur, Chennai (IN); Madhavan Srinivasan, Chennai (IN); Neelakandan Narayanan Chulliel, Chennai (IN); Haridas Sankar, Chennai (IN); Kausik Ghosh, Chennai (IN)

( * ) Notice: Subject to any disclaimer, the term of this patent is extended or adjusted under 35 U.S.C. 154(b) by 439 days.

This patent is subject to a terminal disclaimer.

(21) Appl. No.: 13/144,932

(22) PCT Filed: Jan. 20, 2010

(86) PCT No.: PCT/IB2010/050242
§ 371 (c)(1), (2), (4) Date: Jul. 18, 2011

(87) PCT Pub. No.: WO2010/084457
PCT Pub. Date: Jul. 29, 2010

(65) Prior Publication Data
US 2011/0281830 A1    Nov. 17, 2011

(30) Foreign Application Priority Data
Jan. 21, 2009    (IN) .......................... 134/MUM/2009

(51) Int. Cl.
*A61K 31/56*    (2006.01)
*A61K 9/06*    (2006.01)
*A61K 9/00*    (2006.01)

(52) U.S. Cl.
CPC .............. *A61K 9/06* (2013.01); *A61K 9/0014* (2013.01); *A61K 31/56* (2013.01)

(58) Field of Classification Search
CPC ........ A61K 9/06; A61K 9/0014; A61K 31/56
USPC .................................. 514/182, 170
See application file for complete search history.

(56) References Cited

U.S. PATENT DOCUMENTS 6,635,702 B1 * 10/2003 Schmucker-Castner et al. ......................... 524/291
2011/0257144 A1 10/2011 Vanangamudi et al.

FOREIGN PATENT DOCUMENTS

WO   WO/2007/087806    8/2007

OTHER PUBLICATIONS

Fucibet Lipid cream monograph, 2007.*
Fucicort monograph, Sep. 2007.*
English translation of Fucicort monograph, Sep. 2007.*
Remington Pharmaceutical Science, 17th ed., 1985, pp. 1278-1279.*
References Which Form a Part of the ISR Report are not Repeated Here.

* cited by examiner

*Primary Examiner* — San-Ming Hui

(57) ABSTRACT

The invention discloses a dermaceutical cream containing steroids and an antibacterial agent in the form of Fusidic acid, which Fusidic acid is formed in situ from Sodium Fusidate as the starting raw material, wherein Sodium Fusidate is converted into Fusidic acid under oxygen-free environment. The cream of the present invention has greater shelf-life stability and the finer particle size of the API than the conventional creams containing Fusidic acid. The cream of the present invention contains Fusidic acid as the API that has been formed in situ from Sodium Fusidate, and steroids in a cream base comprising an acid, a co-solvent, an emulsifier and a waxy material along with water, preferably purified water.

16 Claims, No Drawings

DERMACEUTICAL CREAM MADE USING SODIUM FUSIDATE AND STEROIDS

FIELD OF INVENTION

The present invention relates to primary & secondary bacterial skin infections and inflammations and in particular it relates to the single dose treatment using a steroids cream that also contains an antibacterial agent in the form of a Fusidic acid wherein the Fusidic acid has been made using Sodium Fusidate as the starting Active Pharmaceutical Ingredient (API).

BACKGROUND OF THE INVENTION

Use of steroids to alleviate inflammation, irritation and itching caused by skin ailments is well known. It is also well known that use of steroids compromises patient's immune system and exposes them to bacterial infections. Single dose therapies containing steroids and antibacterials are well known.

Numerous single dose treatments, both topical and systemic, are currently employed for the treatment of above skin inflammations. Topical and systemic inflammatory treatment compositions typically employ a combination of corticosteroids in a base component. The active ingredients typically comprise Corticosteroids such as steroids like Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like.

Numerous treatments, both topical and systemic, are available for the primary and secondary skin infection caused by sensitive Gram +ve organisms such as *Staphylococcus aureus, Streptococcus* spp etc. Topical and systemic bacterial infection treatment compositions typically employ at least one active pharmaceutical ingredient (API) in combination with a base component. In the cream form, the APIs typically comprise an antibiotic/antibacterial such as Fusidic acid and the like.

In the currently available Fusidic acid creams, Fusidic acid in fine powder form is used as source API. The small particle size enhances its dermal contact by providing a large specific surface area and penetration, and provides a smooth feel on application to skin. However, a serious shortcoming of the fine size of Fusidic acid particles is that it presents an enormous surface area for contact and reaction with molecular Oxygen during manufacture, handling, and processing of the cream. This has serious implications to its chemical stability and results in rapid reduction in potency of the API (Fusidic acid) in the final cream formulation. Degradation due to oxidation is a major cause of instability of currently available Fusidic acid creams. Table 1 show that the degradation in the API samples (Fusidic acid) exposed to oxygen ranged between 7.7% and 11% for conditions ranging from room temperature to 45° C. when analysed at three months of exposure period at the above conditions.

It is known that greater the exposure time of Fusidic acid as the raw API to Oxygen, greater the limitations on stabilising Fusidic acid in a formulation. However, there is no published data on the stability of Fusidic acid over a period of time.

As an alternative to Fusidic acid, Sodium Fusidate is known to have been used to make dermaceutical medicaments for topical application. However, these are in the form of ointment rather than cream. Drawbacks of ointments over creams are well known and it's generally preferable to use creams rather than ointments for topical application.

Several aspects of Fusidic acid as an API are known:
It is thermolabile
It is available in cream formulations
It can be obtained from Sodium Fusidate by dissolving the latter in an aqueous phase and adding acid to the solution, whereby Fusidic acid precipitates. However, the Fusidic acid precipitate is difficult to process into a cream form first due to its coarse and uneven particle size and second retrieving Fusidic acid from wet cake involves drying and further handling which deteriorates the Fusidic acid due to exposure to oxygen
The stability of the API in a Fusidic acid cream is unreliable due to the thermolabile nature of Fusidic acid
Stabilization of medicaments containing Fusidic acid against oxidation involves observing a number of stringent precautionary procedures during manufacture and storage. These include:
replacing Oxygen in pharmaceutical containers with inert gases such as Nitrogen, Carbon dioxide, Helium and the like
avoiding contact of the medicament with heavy metal ions which catalyze oxidation,
storing the API at reduced temperatures throughout its shelf life before processing
In practice this means stricter controls during the manufacture as well as storage of such API (storing it typically at 2° C. to 8° C. in air-tight containers throughout their shelf life).

There is therefore a need to provide a Fusidic acid cream in which Fusidic acid will be of greater stability at the time of the manufacture of the cream, and which will sustain its stability at an acceptable level throughout its shelf life.

There's a need to provide dermaceutical cream containing steroids, and an antibacterial in the form of Fusidic acid, and in which Fusidic acid will be of greater stability at the time of the manufacture of the cream, and which will sustain its stability at an acceptable level throughout its shelf life.

OBJECTS AND ADVANTAGES OF THE INVENTION

It is therefore one object of the present invention to provide a cream which contains Fusidic acid as the active API but which has greater stability of the API throughout its shelf life.

It is a further objective of the present invention to provide a dermaceutical cream containing at least one steroid, and an antibacterial agent in the form of Fusidic acid, in which Fusidic acid will be of greater stability at the time of the manufacture of the cream, and which will sustain its stability at an acceptable level throughout its shelf life.

BRIEF SUMMARY OF THE INVENTION

The invention discloses a dermaceutical cream containing steroids such as Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like, and an antibacterial agent in the form of Fusidic acid, which Fusidic acid is formed in situ from Sodium Fusidate as the starting raw material, wherein Sodium Fusidate is converted into Fusidic acid under oxygen-free environment. The cream of the present invention has greater shelf-life stability and the finer particle size of the API than the conventional creams containing Fusidic acid. The cream of the present invention contains Fusidic acid as the API that has been formed in situ from Sodium Fusidate, and steroids such as Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like in a cream base comprising an acid, a co-solvent, an emulsifier and a waxy material along with water, preferably purified water.

DETAILED DESCRIPTION OF THE INVENTION

We discussed earlier the known aspects of the topical preparations that have Fusidic acid and Sodium Fusidate as the APIs. It is evident from the current state of knowledge that:

Creams containing Fusidic acid that are made using Sodium Fusidate as starting API are not available.

Creams containing Fusidic acid that are made using Sodium Fusidate along with steroids such as Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like as starting APIs are not available.

There is no published data on the stability of Sodium Fusidate as the API.

Sodium Fusidate is not considered to be inherently more stable as an API than Fusidic acid.

In the face of this, it has been surprisingly discovered that Sodium Fusidate as an API is significantly more stable than Fusidic acid and that Fusidic acid deteriorates more rapidly than Sodium Fusidate.

There is no published data on the stability of Sodium Fusidate as the API. The applicant carried out experiments on Sodium Fusidate to evaluate its stability. It can be seen from Table 2 that the degradation of Sodium Fusidate over a temperature range of room temperature to 45° C. ranged between 2.45% and 6%.

Tables 1 and 2 also show the comparison between the stability of the Fusidic acid and Sodium Fusidate as raw APIs. The study was carried out using an in-house HPLC method developed by the applicant, which the applicant believes is a true stability-indicating method as opposed to the titration method suggested in British Pharmacopoeia (BP). This is because the BP method does not differentiate between the intact API and the degraded form.

Stability Analysis of Fusidic Acid

TABLE 1

Results Of 3 Months Old Fusidic Acid (API) Analysis By Stability Indicating HPLC Method And Titration Method
Name of Sample: FUSIDIC ACID BP;
Pack: Open (O) & Closed (C) Petri dish

| S. No | Conditions | *Initial (%) | Fusidic Acid Assay (%) | | Percentage Drop (%) | | Remarks |
|---|---|---|---|---|---|---|---|
| | | | Titration | HPLC | Titration | HPLC | |
| 1 | RT (O) | 100.6 | 99.21 | 92.93 | 1.39 | 7.67 | API |
| 2 | RT (C) | | 99.02 | 94.37 | 1.58 | 6.23 | analysed |
| 3 | 45° C. (O) | | 98.52 | 89.52 | 2.08 | 11.08 | After 3 |
| 4 | 45° C. (C) | | 99.10 | 92.12 | 1.50 | 8.48 | Months |

Stability Analysis of Sodium Fusidate

TABLE 2

Results Of 3 Months Old Sodium Fusidate (API) Analysis By Stability Indicating HPLC Method And Titration Method
Name of the Sample: Sodium Fusidate BP
Pack: Open & Closed Petri dish

| S. No | Conditions | *Initial (%) | Sodium Fusidate Assay (%) | | Percentage (%) | | Remarks |
|---|---|---|---|---|---|---|---|
| | | | Titration | HPLC | Titration | HPLC | |
| 1 | RT (O) | 98.7 | 97.71 | 96.25 | 0.99 | 2.45 | API |
| 2 | RT (C) | | 98.85 | 97.67 | −0.15 | 1.03 | analysed |
| 3 | 45° C. (O) | | 97.07 | 92.65 | 1.63 | 6.05 | After 3 |
| 4 | 45° C. (C) | | 97.16 | 92.96 | 1.54 | 5.74 | Months |

In both studies the * Initial denotes the results of the samples tested at the time of receipt of the API from the supplier.

It can be observed from Tables 1 and 2 that:

In the case of Fusidic Acid, there is about 7.7% loss in 3 Months at room temperature (open condition) and about 11% loss in 3 Months at 45° C. (open condition).

In the case of Sodium Fusidate, there is about 2.5% loss in 3 Months at room temperature (open condition) and about 6% loss in 3 Months at 45° C. (open condition).

The data thus shows that Sodium Fusidate as an API is more stable than Fusidic acid.

The applicant explored the possibility of making a cream (rather than an ointment) using Sodium Fusidate (rather than Fusidic acid) and steroids such as Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like. Although Sodium Fusidate has been used in dermaceutical applications, it has not been possible to make creams that use Sodium Fusidate. This is because of the inherent alkalinity of Sodium Fusidate (pH 7.5 to 9), which means it cannot be used in a cream form therefore all products manufactured using Sodium Fusidate as starting material are ointments. A dermaceutical cream that uses Sodium Fusidate and steroids would exploit the benefit of the fact that Sodium Fusidate is more stable than Fusidic acid and it would also provide a cream formulation which is far superior in its application qualities than an ointment. It would thus fill an existing need for a cream that has better stability than currently available creams containing Fusidic acid and steroids.

The applicant therefore surprisingly discovered that in order to achieve greater stability of the API in a dermaceutical cream, Sodium Fusidate rather than Fusidic acid may be used as the starting API during the cream's manufacture. Using Sodium Fusidate as starting material eliminates the drawback associated with the manufacture and storage of existing Fusidic acid creams.

The applicant has also discovered that the Fusidic acid and Steroids cream prepared using Sodium Fusidate as the starting APIs showed good chemical stability, and efficacy, The application discloses a cream containing Steroids such as Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like and Fusidic acid (the API) that has been prepared using Sodium Fusidate as the starting API, in which Fusidic acid forms in-situ under totally oxygen free environment by slow addition of an acid, into a molecular dispersion form (due to the presence of a co-solvent) at the intermediate stage, and which Fusidic acid regenerates as an extremely fine dispersion when added to a final cream base, thereby resulting in a finely and homogeneously dispersed Fusidic acid in the final cream. All these operations are performed in an environment free of atmospheric oxygen. The cream of the present invention contains Fusidic acid as the API that has been formed in situ from Sodium Fusidate, steroids such as Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like in a cream base comprising an acid, a co-solvent, an emulsifier and a waxy material along with water, preferably purified water.

The APIs which may be employed in the present invention as starting APIs are either acid-based actives or their salts well known in the art of treating bacterial primary & secondary infections and inflammations. Examples of suitable acid-based actives or their salts which may be used include, but are not limited to Sodium Fusidate and steroids such as Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like.

These acid-based active compounds or their salts require a base component to be used in the pharmaceutical composition that uses the compounds, since the compounds cannot, by themselves, be deposited directly on to human skin due to their harshness.

The cream base of the present invention optionally further comprises an ingredient selected from a group comprising a preservative, a buffering agent, an anti oxidant, a chelating agent, and a humectant, or any combination thereof.

The present invention provides a novel cream that has been produced using Sodium Fusidate as the starting raw material, and which cream contains Fusidic acid of high therapeutic efficacy and of chemical stability that is generally superior to the commercially available creams containing Fusidic acid.

The Fusidic acid and steroids cream of the present invention has been manufactured in a totally oxygen free environment under purging with inert gas and applying vacuum. Under these conditions, the Sodium Fusidate is converted in situ into Fusidic acid. The cream of the present invention is used in the treatment of bacterial skin infections and inflammations.

The pH of the product of the present invention is from about 3 to 6. On the other hand, Sodium Fusidate ointments that are commercially available are greasy and cosmetically non elegant.

It is essential that the active drug penetrates the skin for the optimum bio-dermal efficacy. The particle size of the active drug plays an important role here. It is necessary that the active drug is available in a finely dispersed form for the product to be being efficacious. Also this is to be achieved in the safe pH compatible environment of skin (4.0 to 6.0). To achieve all these, it is essential to choose proper vehicles or co-solvents for the dissolution or dispersion of the drug.

The product of the present invention is efficacious due to the pronounced anti-inflammatory, antibacterial activity of the steroids and regenerated Fusidic acid which is available in reduced particle size than the conventional products, and in a finely dispersed form.

The inventor has screened different co-solvents such as Propylene Glycol, Hexylene Glycol, PolyEthyleneGlycol-400 & the like and dissolved the Sodium Fusidate in one of above co-solvents varying from about 5% (w/w) to 40% (w/w) under inert gas purging and under vacuum and converted to Fusidic acid in-situ by adding an acid such as HCl, $H_2SO_4$, $HNO_3$, Lactic acid and the like from about 0.005% (w/w) to about 0.5% (w/w) under stirring and obtained Fusidic acid in more stabilized and solution form, which makes our final product in a cream base which easily penetrates the skin and highly efficacious, and also highly derma compatible by having a pH of about 3.0 to about 6.0.

The stability of the product is confirmed by the stability studies performed for 3/6 months as per ICH guidelines.

Experimental Data

APIs-stability experiments were carried out (see tables 3-20) using several products that are representative of the present invention. Tests were carried out to observe (or measure as appropriate) the physical appearance of the product, the pH value and assay of the APIs over a period of time. Each gram of product of the present invention used for the tests contained Sodium Fusidate in the amount required to produce 2% (w/w) Fusidic acid in the finished product and appropriate amount of steroids as mentioned below i. Betamethasone Valerate—0.12% (w/w)
   ii. Fluticasone Propionate—0.05% (w/w)
   iii. Mometasone Furoate—0.1% (w/w)
   iv. Dexamethasone Acetate—0.1% (w/w)
   v. Hydrocortisone Acetate—1.0% (w/w)
   vi. Clobetasol Propionate—0.05% (w/w)
   vii. Beclomethasone Dipropionate—0.025% (w/w)
   viii. Betamethasone Dipropionate—0.05% (w/w)

wherein all percentages are with respect to the final formulation.

The product used for the Stability Studies tests contained approximately 10% extra APIs (overages). It was packaged in an aluminium collapsible tube and each gram of the product contained 20.8 mg of Sodium Fusidate (in conformance with BP), which is equivalent to 20 mg of Fusidic acid (BP conformant).

i) Product: Sodium Fusidate+Betamethasone Valerate Cream
PACK: Aluminum Collapsible Tube

| Composition: Each gm contains: | | |
|---|---|---|
| i) Sodium Fusidate BP Equivalent to Fusidic Acid | BP | 2.0% |
| ii) Betamethasone Valerate | IP | 0.12% |

TABLE 3

Description Test, Batch No. SBV-01
Measured parameter: Physical appearance
Best value of measured parameter: Homogeneous White to off White Viscous cream
Method of measurement: Observation by naked eye

| Conditions | Initial | 1st Month | 2nd Month | 3rd Month |
|---|---|---|---|---|
| 40° C. 75% RH | Homogenous White to off White viscous cream | Homogenous White to off White viscous cream | Homogenous White to off White viscous cream | Homogenous White to off White viscous cream |
| 30° C. 65% RH | — | Homogenous White to off White viscous cream | Homogenous White to off White viscous cream | Homogenous White to off White viscous cream |

TABLE 3-continued

Description Test, Batch No. SBV-01
Measured parameter: Physical appearance
Best value of measured parameter: Homogeneous White to off White Viscous cream
Method of measurement: Observation by naked eye

| Conditions | Initial | 1st Month | 2nd Month | 3rd Month |
|---|---|---|---|---|
| 25° C. 60% RH | — | Homogenous White to off White viscous cream | Homogenous White to off White viscous cream | Homogenous White to off White viscous cream |
| Temperature cycling | — | Homogenous White to off White viscous cream | — | — |
| Freezthaw | — | Homogenous White to off White viscous cream | — | — |

TABLE 4 pH Test, Batch No. SBV-01
Measured parameter: pH; Limits of measured parameter: 3-6
Method of measurement: Digital pH Meter

| Conditions | Initial | 1st Month | 2nd Month | 3rd Month |
|---|---|---|---|---|
| 40° C. 75% RH | 4.25 | 4.24 | 4.23 | 4.24 |
| 30° C. 65% RH | — | 4.23 | 4.24 | 4.23 |
| 25° C. 60% RH | — | 4.24 | 4.23 | 4.24 |
| Temperature cycling | — | 4.23 | — | — |
| Freezthaw | — | 4.22 | — | — |

TABLE 5

Assay (%) Test, Batch No. SBV-01
Measured parameter: Assay (%); Limits of measured parameter: 90-110
Method of measurement: HPLC Method

| Conditions | Assay (%) | Initial | 1st Month | 2nd Month | 3rd Month |
|---|---|---|---|---|---|
| 40° C. 75% RH | i) Fusidic acid | 108.57 | 108.46 | 108.16 | 108.11 |
| | ii) Betamethasone Valerate | 109.56 | 109.51 | 109.32 | 109.11 |
| 30° C. 65% RH | i) Fusidic acid | — | 108.53 | 108.41 | 108.36 |
| | ii) Betamethasone Valerate | | 109.48 | 109.42 | 109.20 |
| 25° C. 60% RH | i) Fusidic acid | — | 108.54 | 108.42 | 108.40 |
| | ii) Betamethasone Valerate | | 109.54 | 109.42 | 109.21 |
| Temperature cycling | i) Fusidic acid | — | 107.53 | — | — |
| | ii) Betamethasone Valerate | | 109.51 | | |
| Freezthaw | i) Fusidic acid | — | 108.01 | — | — |
| | ii) Betamethasone Valerate | | 108.25 | | | ii) Product: sodium Fusidate+Fluticasone Propionate Cream
PACK: Aluminum Collapsible Tube

| Composition: Each gm contains: | | |
|---|---|---|
| i) Sodium Fusidate BP Equivalent to Fusidic Acid | BP | 2.0% |
| ii) Fluticasone Propionate | BP | 0.05% |

TABLE 6

Description Test, Batch No. SFC-01
Measured parameter: Physical appearance
Best value of measured parameter: Homogeneous White to off White Viscous cream
Method of measurement: Observation by naked eye

| Conditions | Initial | 1st Month | 2nd Month | 3rd Month | 6th Month |
|---|---|---|---|---|---|
| 40° C. 75% RH | Homogenous White to off White viscous cream | Homogenous White to off White viscous cream | Homogenous White to off White viscous cream | Homogenous White to off White viscous cream | Homogenous White to off White viscous cream |
| 30° C. 65% RH | — | Homogenous White to off White viscous cream | Homogenous White to off White viscous cream | Homogenous White to off White viscous cream | Homogenous White to off White viscous cream |
| 25° C. 60% RH | — | Homogenous White to off White viscous cream | Homogenous White to off White viscous cream | Homogenous White to off White viscous cream | Homogenous White to off White viscous cream |
| Temperature cycling | — | Homogenous White to off White viscous cream | — | — | — |

TABLE 6-continued

Description Test, Batch No. SFC-01
Measured parameter: Physical appearance
Best value of measured parameter: Homogeneous White to off White Viscous cream
Method of measurement: Observation by naked eye

| Conditions | Initial | 1st Month | 2nd Month | 3rd Month | 6th Month |
|---|---|---|---|---|---|
| Freezthaw | — | Homogenous White to off White viscous cream | — | — | — |

TABLE 7 pH Test, Batch No. SFC-01
Measured parameter: pH; Limits of measured parameter: 3-6; Method of measurement: Digital pH Meter

| Conditions | Initial | 1st Month | 2nd Month | 3rd Month | 6th Month |
|---|---|---|---|---|---|
| 40° C. 75% RH | 3.51 | 3.50 | 3.48 | 3.49 | 3.48 |
| 30° C. 65% RH | — | 3.50 | 3.49 | 3.48 | 3.47 |
| 25° C. 60% RH | — | 3.51 | 3.49 | 3.50 | 3.49 |
| Temperature cycling | — | 3.49 | — | — | — |
| Freezthaw | — | 3.48 | — | — | — |

TABLE 8

Assay (%) Test, Batch No. SFC-01
Measured parameter: Assay (%)
Limits of measured parameter: 90-110
Method of measurement: HPLC Method

| Conditions | Assay (%) | Initial | 1st Month | 2nd Month | 3rd Month | 6th Month |
|---|---|---|---|---|---|---|
| 40° C. 75% RH | i) Fusidic acid | 108.68 | 108.56 | 108.36 | 108.21 | 108.18 |
| | ii) Fluticasone Propionate | 108.56 | 108.51 | 108.32 | 108.11 | 108.08 |
| 30° C. 65% RH | i) Fusidic acid | — | 108.53 | 108.31 | 108.26 | 108.22 |
| | ii) Fluticasone Propionate | | 108.48 | 108.42 | 108.20 | 108.11 |
| 25° C. 60% RH | i) Fusidic acid | — | 108.64 | 108.52 | 108.48 | 108.38 |
| | ii) Fluticasone Propionate | | 108.54 | 108.42 | 108.21 | 108.10 |
| Temperature cycling | i) Fusidic acid | — | 108.10 | — | — | — |
| | ii) Fluticasone Propionate | | 108.51 | — | — | — |
| Freezthaw | i) Fusidic acid | — | 108.21 | — | — | — |
| | ii) Fluticasone Propionate | | 108.15 | — | — | — | iii) Product: Sodium Fusidate+Mometasone Furoatecream
PACK: Aluminum Collapsible Tube

| Composition: | Each gm contains: |
|---|---|
| i) Sodium Fusidate BP Equivalent to Fusidic Acid BP | 2.0% |
| ii) Mometasone Furoate USP | 0.1% |

TABLE 9

Description Test, Batch No. SFM-01
Measured parameter: Physical appearance
Best value of measured parameter: Homogeneous White to off White Viscous cream;
Method of measurement: Observation by naked eye

| Conditions | Initial | 1st Month | 2nd Month | 3rd Month | 6th Month |
|---|---|---|---|---|---|
| 40° C. 75% RH | Homogenous White to off White viscous cream | Homogenous White to off White viscous cream | Homogenous White to off White viscous cream | Homogenous White to off White viscous cream | Homogenous White to off White viscous cream |

TABLE 9-continued

Description Test, Batch No. SFM-01
Measured parameter: Physical appearance
Best value of measured parameter: Homogeneous
White to off White Viscous cream;
Method of measurement: Observation by naked eye

| Conditions | Initial | 1st Month | 2nd Month | 3rd Month | 6th Month |
|---|---|---|---|---|---|
| 30° C. 65% RH | — | Homogenous White to off White viscous cream | Homogenous White to off White viscous cream | Homogenous White to off White viscous cream | Homogenous White to off White viscous cream |
| 25° C. 60% RH | — | Homogenous White to off White viscous cream | Homogenous White to off White viscous cream | Homogenous White to off White viscous cream | Homogenous White to off White viscous cream |
| Temperature cycling | — | Homogenous White to off White viscous cream | — | — | — |
| Freezthaw | — | Homogenous White to off White viscous cream | — | — | — |

TABLE 10 pH Test, Batch No. SFM-01
Measured parameter: pH;
Limits of measured parameter: 3-6
Method of measurement: Digital pH Meter

| Conditions | Initial | 1st Month | 2nd Month | 3rd Month | 6th Month |
|---|---|---|---|---|---|
| 40° C. 75% RH | 3.54 | 3.53 | 3.52 | 3.53 | 3.52 |
| 30° C. 65% RH | — | 3.52 | 3.53 | 3.54 | 3.53 |
| 25° C. 60% RH | — | 3.53 | 3.54 | 3.53 | 3.52 |
| Temperature cycling | — | 3.52 | — | — | — |
| Freezthaw | — | 3.53 | — | — | — |

TABLE 11

Assay (%) Test, Batch No. SFM-01
Measured parameter: Assay (%)
Limits of measured parameter: 90-110;
Method of measurement: HPLC Method

| Conditions | Assay (%) | Initial | $1^{st}$ Month | $2^{nd}$ Month | $3^{rd}$ Month | $6^{th}$ Month |
|---|---|---|---|---|---|---|
| 40° C. 75% RH | i) Fusidic acid | 108.27 | 108.26 | 108.14 | 108.08 | 107.89 |
|  | ii) Mometasone Furoate | 108.56 | 108.51 | 108.32 | 108.11 | 107.88 |
| 30° C. 65% RH | i) Fusidic acid | — | 108.23 | 108.21 | 108.16 | 107.92 |
|  | ii) Mometasone Furoate | — | 108.48 | 108.42 | 108.20 | 107.75 |
| 25° C. 60% RH | i) Fusidic acid | — | 108.24 | 108.22 | 108.20 | 107.95 |
|  | ii) Mometasone Furoate | — | 108.54 | 108.42 | 108.21 | 107.82 |
| Temperature cycling | i) Fusidic acid | — | 107.63 | — | — | — |
|  | ii) Mometasone Furoate | — | 108.51 | — | — | — |
| Freezthaw | i) Fusidic acid | — | 108.11 | — | — | — |
|  | ii) Mometasone Furoate | — | 108.15 | — | — | — | iv) Product: Sodium Fusidate+Dexamethasone Acetate Cream
PACK: Aluminum Collapsible Tube

| Composition: | Each gm contains: |
|---|---|
| i) Sodium Fusidate BP Equivalent to Fusidic Acid BP | 2.0% |
| ii) Dexamethasone Acetate IP | 0.1% |

TABLE 12

Description Test, Batch No. SFD-01
Measured parameter: Physical appearance
Best value of measured parameter: Homogeneous White to off White Viscous cream
Method of measurement: Observation by naked eye

| Conditions | Initial | 1st Month | 2nd Month | 3rd Month |
| --- | --- | --- | --- | --- |
| 40° C. 75% RH | Homogenous White to off White viscous cream | Homogenous White to off White viscous cream | Homogenous White to off White viscous cream | Homogenous White to off White viscous cream |
| 30° C. 65% RH | — | Homogenous White to off White viscous cream | Homogenous White to off White viscous cream | Homogenous White to off White viscous cream |
| 25° C. 60% RH | — | Homogenous White to off White viscous cream | Homogenous White to off White viscous cream | Homogenous White to off White viscous cream |
| Temperature cycling | — | Homogenous White to off White viscous cream | — | — |
| Freezthaw | — | Homogenous White to off White viscous cream | — | — |

TABLE 13 pH Test, Batch No. SFD-01
Measured parameter: pH
Limits of measured parameter: 3-6
Method of measurement: Digital pH Meter

| Conditions | Initial | 1st Month | 2nd Month | 3rd Month |
| --- | --- | --- | --- | --- |
| 40° C. 75% RH | 4.22 | 4.21 | 4.20 | 4.20 |
| 30° C. 65% RH | — | 4.22 | 4.21 | 4.20 |
| 25° C. 60% RH | — | 4.21 | 4.21 | 4.20 |
| Temperature cycling | — | 4.21 | — | — |
| Freezthaw | — | 4.20 | — | — |

TABLE 14

Assay (%) Test, Batch No. SFD-01
Measured parameter: Assay (%);
Limits of measured parameter: 90-110
Method of measurement: HPLC Method

| Conditions | Assay (%) | Initial | 1st Month | 2nd Month | 3rd Month |
| --- | --- | --- | --- | --- | --- |
| 40° C. 75% RH | i) Fusidic acid | 108.62 | 108.58 | 108.44 | 108.30 |
| | ii) Dexamethasone Acetate | 108.15 | 108.14 | 108.12 | 108.05 |
| 30° C. 65% RH | i) Fusidic acid | — | 108.63 | 108.52 | 108.32 |
| | ii) Dexamethasone Acetate | | 108.14 | 108.12 | 108.09 |
| 25° C. 60% RH | i) Fusidic acid | — | 108.60 | 108.54 | 108.46 |
| | ii) Dexamethasone Acetate | | 108.14 | 108.11 | 108.10 |
| Temperature cycling | i) Fusidic acid | | 108.52 | — | — |
| | ii) Dexamethasone Acetate | | 107.68 | — | — |
| Freezthaw | i) Fusidic acid | — | 108.41 | — | — |
| | ii) Dexamethasone Acetate | — | 107.84 | — | — | v) Product: Sodium Fusidate+Hydrocortisone Acetate Cream
PACK: Aluminum Collapsible Tube

| Composition: | Each gm contains: |
| --- | --- |
| i) Sodium Fusidate BP Equivalent to Fusidic Acid BP | 2.0% |
| ii) Hydrocortisone Acetate IP | 1.0% |

TABLE 15

Description Test, Batch No. HAS-01
Measured parameter: Physical appearance
Best value of measured parameter: Homogeneous White to off White Viscous cream;
Method of measurement: Observation by naked eye

| Conditions | Initial | 1st Month | 2nd Month | 3rd Month |
| --- | --- | --- | --- | --- |
| 40° C. 75% RH | Homogenous White to off White viscous cream | Homogenous White to off White viscous cream | Homogenous White to off White viscous cream | Homogenous White to off White viscous cream |
| 30° C. 65% RH | — | Homogenous White to off White viscous cream | Homogenous White to off White viscous cream | Homogenous White to off White viscous cream |
| 25° C. 60% RH | — | Homogenous White to off White viscous cream | Homogenous White to off White viscous cream | Homogenous White to off White viscous cream |
| Temp cycling | — | Homogenous White to off White viscous cream | — | — |
| Freezthaw | — | Homogenous White to off White viscous cream | — | — |

TABLE 16 pH Test, Batch No. HAS-01
Measured parameter: pH
Limits of measured parameter: 3-6
Method of measurement: Digital pH Meter

| Conditions | Initial | 1st Month | 2nd Month | 3rd Month |
|---|---|---|---|---|
| 40° C. 75% RH | 4.31 | 4.30 | 4.29 | 4.28 |
| 30° C. 65% RH | — | 4.31 | 4.30 | 4.29 |
| 25° C. 60% RH | — | 4.30 | 4.29 | 4.28 |
| Temperature cycling | — | 4.29 | — | — |
| Freezthaw | — | 4.28 | — | — |

TABLE 17

Assay (%) Test, Batch No. HAS-01
Measured parameter: Assay (%)
Limits of measured parameter: 90-110
Method of measurement: HPLC Method

| Conditions | Assay (%) | Initial | 1st Month | 2nd Month | 3rd Month |
|---|---|---|---|---|---|
| 40° C. 75% RH | i) Fusidic acid | 108.52 | 108.48 | 108.34 | 108.20 |
|  | ii) Hydrocortisone Acetate | 107.15 | 107.14 | 107.12 | 107.05 |
| 30° C. 65% RH | i) Fusidic acid | — | 108.51 | 108.42 | 108.32 |
|  | ii) Hydrocortisone Acetate | — | 107.14 | 107.12 | 107.09 |
| 25° C. 60% RH | i) Fusidic acid | — | 108.50 | 108.44 | 108.36 |
|  | ii) Hydrocortisone Acetate | — | 107.14 | 107.11 | 107.10 |
| Temperature cycling | i) Fusidic acid | — | 108.40 | — | — |
|  | ii) Hydrocortisone Acetate | — | 107.11 | — | — |
| Freezthaw | i) Fusidic acid | — | 108.31 | — | — |
|  | ii) Hydrocortisone Acetate | — | 107.14 | — | — |

Vi) Product: Sodium Fusidate+Clobetasol Propionate Cream
PACK: Aluminum Collapsible Tube

| Composition: | Each gm contains: |
|---|---|
| i) Sodium Fusidate BP Equivalent to Fusidic Acid BP | 2.0% |
| ii) Clobetasol Propionate USP | 0.05% |

TABLE 18

Description Test, Batch No. SPC-01
Measured parameter: Physical appearance
Best value of measured parameter: Homogeneous White to off White Viscous cream
Method of measurement: Observation by naked eye

| Conditions | Initial | 1st Month | 2nd Month | 3rd Month | 6th Month |
|---|---|---|---|---|---|
| 40° C. 75% RH | Homogenous White to off White viscous cream | Homogenous White to off White viscous cream | Homogenous White to off White viscous cream | Homogenous White to off White viscous cream | Homogenous White to off White viscous cream |
| 30° C. 65% RH | — | Homogenous White to off White viscous cream | Homogenous White to off White viscous cream | Homogenous White to off White viscous cream | Homogenous White to off White viscous cream |
| 25° C. 60% RH | — | Homogenous White to off White viscous cream | Homogenous White to off White viscous cream | Homogenous White to off White viscous cream | Homogenous White to off White viscous cream |
| Temp cycling | — | Homogenous White to off White viscous cream | — | — | — |
| Freezthaw | — | Homogenous White to off White viscous cream | — | — | — |

TABLE 19 pH Test, Batch No. SPC-01
Measured parameter: pH
Limits of measured parameter: 3-6
Method of measurement: Digital pH Meter

| Conditions | Initial | 1st Month | 2nd Month | 3rd Month | 6th Month |
|---|---|---|---|---|---|
| 40° C. 75% RH | 4.22 | 4.21 | 4.20 | 4.20 | 4.19 |
| 30° C. 65% RH | — | 4.21 | 4.20 | 4.19 | 4.18 |
| 25° C. 60% RH | — | 4.22 | 4.21 | 4.20 | 4.20 |
| Temp cycling | — | 4.20 | — | — | — |
| Freezthaw | — | 4.19 | — | — | — |

TABLE 20

Assay (%) Test, Batch No. SPC-01
Measured parameter: Assay (%);
Limits of measured parameter: 90-110
Method of measurement: HPLC Method

| Conditions | Assay (%) | Initial | 1st Month | 2nd Month | 3rd Month | 6th Month |
|---|---|---|---|---|---|---|
| 40° C. 75% RH | i) Fusidic acid | 108.38 | 108.33 | 108.24 | 108.10 | 108.01 |
|  | ii) Clobetasol Propionate | 107.41 | 107.34 | 107.22 | 107.15 | 107.10 |

TABLE 20-continued

Assay (%) Test, Batch No. SPC-01
Measured parameter: Assay (%);
Limits of measured parameter: 90-110
Method of measurement: HPLC Method

| Conditions | Assay (%) | Initial | 1st Month | 2nd Month | 3rd Month | 6th Month |
|---|---|---|---|---|---|---|
| 30° C. 65% RH | i) Fusidic acid | — | 108.31 | 108.32 | 108.22 | 108.11 |
|  | ii) Clobetasol Propionate | — | 107.38 | 107.32 | 107.29 | 107.22 |
| 25° C. 60% RH | i) Fusidic acid | — | 108.30 | 108.24 | 108.15 | 108.08 |
|  | ii) Clobetasol Propionate | — | 107.40 | 107.34 | 107.30 | 107.24 |
| Temperature cycling | i) Fusidic acid | — | 108.28 | — | — | — |
|  | ii) Clobetasol Propionate | — | 107.21 | — | — | — |
| Freezthaw | i) Fusidic acid | — | 108.22 | — | — | — |
|  | ii) Clobetasol Propionate | — | 107.11 | — | — | — | vii) Product: Sodium Fusidate+Beclomethasone Dipropionate Cream

PACK: Aluminum Collapsible Tube

| Composition: | Each gm contains: |
|---|---|
| i) Sodium Fusidate BP (Equivalent to Fusidic Acid BP) | 2.0% |
| ii) Beclomethasone dipropionate IP | 0.025% |

TABLE 21

Description Test, Batch No. SFB-01
Measured parameter: Physical appearance
Best value of measured parameter: Homogeneous White to off White Viscous cream; Method of measurement: Observation by naked eye

| Conditions | Initial | 1st Month | 2nd Month | 3rd Month |
|---|---|---|---|---|
| 40° C. 75% RH | Homogenous White to off White viscous cream | Homogenous White to off White viscous cream | Homogenous White to off White viscous cream | Homogenous White to off White viscous cream |
| 30° C. 65% RH | — | Homogenous White to off White viscous cream | Homogenous White to off White viscous cream | Homogenous White to off White viscous cream |
| 25° C. 60% RH | — | Homogenous White to off White viscous cream | Homogenous White to off White viscous cream | Homogenous White to off White viscous cream |
| Temp cycling | — | Homogenous White to off White viscous cream | — | — |
| Freezthaw | — | Homogenous White to off White viscous cream | — | — |

TABLE 22 pH Test, Batch No. SFB-01
Measured parameter: pH
Limits of measured parameter: 3-6
Method of measurement: Digital pH Meter

| Conditions | Initial | 1st Month | 2nd Month | 3rd Month |
|---|---|---|---|---|
| 40° C. 75% RH | 4.33 | 4.32 | 4.32 | 4.31 |
| 30° C. 65% RH | — | 4.31 | 4.30 | 4.31 |
| 25° C. 60% RH | — | 4.32 | 4.33 | 4.32 |
| Temperature cycling | — | 4.31 | — | — |
| Freezthaw | — | 4.32 | — | — |

TABLE 23

Assay (%) Test, Batch No. SFB-01
Measured parameter: Assay (%); Limits of measured parameter: 90-110
Method of measurement: HPLC Method

| Conditions | Assay (%) | Initial | 1st Month | 2nd Month | 3rd Month |
|---|---|---|---|---|---|
| 40° C. 75% RH | i) Fusidic acid | 108.28 | 108.25 | 108.20 | 108.12 |
|  | ii) Beclomethasone dipropionate | 108.12 | 108.04 | 107.98 | 107.88 |
| 30° C. 65% RH | i) Fusidic acid | — | 108.25 | 108.22 | 108.18 |
|  | ii) Beclomethasone dipropionate | — | 108.11 | 107.96 | 107.68 |
| 25° C. 60% RH | i) Fusidic acid | — | 108.22 | 108.18 | 108.15 |
|  | ii) Beclomethasone dipropionate | — | 108.05 | 108.00 | 107.90 |
| Temperature cycling | i) Fusidic acid | — | 108.23 | — | — |
|  | ii) Beclomethasone dipropionate | — | 107.68 | — | — |
| Freezthaw | i) Fusidic acid | — | 108.11 | — | — |
|  | ii) Beclomethasone dipropionate | — | 107.58 | — | — | viii) Product: Sodium Fusidate+Betamethasone Dipropionate Cream

PACK: Aluminum Collapsible Tube

| Composition: | Each gm contains: |
|---|---|
| i) Sodium Fusidate BP Equivalent to Fusidic Acid | BP 2.0% |
| ii) Betamethasone dipropionate | USP 0.05% |

TABLE 24

Description Test, Batch No. STD-01
Measured parameter: Physical appearance
Best value of measured parameter: Homogeneous White to off White Viscous cream
Method of measurement: Observation by naked eye

| Conditions | Initial | 1st Month | 2nd Month | 3rd Month |
|---|---|---|---|---|
| 40° C. 75% RH | Homogenous White to off White viscous cream | Homogenous White to off White viscous cream | Homogenous White to off White viscous cream | Homogenous White to off White viscous cream |
| 30° C. 65% RH | — | Homogenous White to off White viscous cream | Homogenous White to off White viscous cream | Homogenous White to off White viscous cream |
| 25° C. 60% RH | — | Homogenous White to off White viscous cream | Homogenous White to off White viscous cream | Homogenous White to off White viscous cream |
| Temperature cycling | — | Homogenous White to off White viscous cream | — | — |
| Freezthaw | — | Homogenous White to off White viscous cream | — | — |

TABLE 25 pH Test, Batch No. STD-01
Measured parameter: pH
Limits of measured parameter: 3-6
Method of measurement: Digital pH Meter

| Conditions | Initial | 1st Month | 2nd Month | 3rd Month |
|---|---|---|---|---|
| 40° C. 75% RH | 4.31 | 4.30 | 4.31 | 4.30 |
| 30° C. 65% RH | — | 4.31 | 4.30 | 4.31 |
| 25° C. 60% RH | — | 4.30 | 4.31 | 4.31 |
| Temperature cycling | — | 4.31 | — | — |
| Freezthaw | — | 4.30 | — | — |

TABLE 26

Assay (%) Test, Batch No. STD-01
Measured parameter: Assay (%)
Limits of measured parameter: 90-110
Method of measurement: HPLC Method

| Conditions | Assay (%) | Initial | 1st Month | 2nd Month | 3rd Month |
|---|---|---|---|---|---|
| 40° C. 75% RH | i) Fusidic acid | 108.82 | 108.78 | 108.70 | 108.52 |
| | ii) Betamethasone dipropionate | 107.52 | 107.44 | 107.38 | 107.28 |
| 30° C. 65% RH | i) Fusidic acid | — | 108.75 | 108.62 | 108.48 |
| | ii) Betamethasone dipropionate | | 107.48 | 107.36 | 107.22 |
| 25° C. 60% RH | i) Fusidic acid | — | 108.62 | 108.58 | 108.45 |
| | ii) Betamethasone dipropionate | | 107.28 | 107.21 | 107.19 |
| Temperature cycling | i) Fusidic acid | — | 108.63 | — | — |
| | ii) Betamethasone dipropionate | | 107.28 | | |
| Freezthaw | i) Fusidic acid | — | 108.41 | — | — |
| | ii) Betamethasone dipropionate | | 107.38 | | |

From the above data, it is evident that product of the present invention is quite stable at ambient conditions and also at elevated temperature & humid conditions of storage.

According to the preferred embodiment of the present invention, there is provided a single dose composition comprising at least one steroid and at least one antibacterial agent for the topical treatment of bacterial skin infections and inflammations on human skin, the composition comprising a steroid selected from a group comprising Betamethasone Valerate, Fluticasone Propionate, Mometasone Furoate, Dexamethasone Acetate, Hydrocortisone Acetate, Clobetasol Propionate, Beclomethasone Dipropionate, Betamethasone Dipropionate and the like, and Fusidic acid made in situ by a conversion of Sodium Fusidate, a cream base containing primary and secondary emulsifiers, waxy materials, co-solvents, and acids, and water.

The proportions of various components of the preferred embodiment are as follows:

a. Fusidic acid from about 0.1% (w/w) to about 25% (w/w) by weight, preferably from about 0.5% (w/w) to about 5% (w/w) by weight and more preferably about 2.00% (w/w), which has been converted in situ from Sodium Fusidate from about 0.1% (w/w) to about 25% (w/w) by weight, preferably from about 0.5% (w/w) to about 5% (w/w) by weight and more preferably about 2.08% (w/w), and from about 0.001% (w/w) to about 5% (w/w) by weight, preferably from about 0.005% (w/w) to about 2.00% (w/w) by weight, and most preferably from about 0.05% (w/w) to 1.0% (w/w) by weight, of a corticosteroid active compound, b. a cream base containing primary and secondary emulsifiers, waxy materials, co-solvents, acids, and water wherein primary and secondary emulsifiers are selected from a group comprising Cetostearyl alcohol, Cetomacrogol-1000, Polysorbate-80, Span-80 and the like from about 1% (w/w) to 15% (w/w), preferably 15% (w/w), more preferably 14.5% (w/w)

waxy materials are selected from a group comprising White Soft Paraffin, Liquid Paraffin, Hard Paraffin and the like from about 5% (w/w) to 20% (w/w), preferably 15% (w/w), more preferably 12.5% (w/w), co-solvents are selected from a group comprising Propylene Glycol, Hexylene Glycol, PolyEthylene Glycol-400 and the like from about 5% (w/w) to 40% (w/w), preferably 30% (w/w), more preferably 25% (w/w), acids are selected from a group comprising HCl, H2So4, HNO3, Lactic acid and the like from about 0.005% (w/w) to 0.5% (w/w), preferably 0.3% (w/w), more preferably 0.25% (w/w), and water in the amount in the range of 20% (w/w) to 75% (w/w), preferably 35% (w/w) to 50% (w/w), more preferably 40% (w/w) to 43% (w/w), preferably purified water.

In another embodiment of the present invention the product of the preferred embodiment is further provided with preservatives, wherein said preservatives are selected from a group comprising Methylparaben, Propylparaben, Chlorocresol, Potassium sorbate, Benzoic acid and the like from about 0.05% (w/w) to 0.5% (w/w), preferably 0.3% (w/w), more preferably 0.2% (w/w).

In a still further embodiment of the present invention, the product of the preferred embodiment is further provided with a buffering agent selected from a group comprising Di Sodium Hydrogen Ortho Phosphate, Sodium Hydrogen Ortho Phosphate and the like from about 0.01% (w/w) to 1.00% (w/w), preferably 0.5% (w/w), more preferably 0.05% (w/w).

In yet another embodiment of the present invention, the product of the preferred embodiment is further provided with an anti oxidants are selected from a group comprising Butylated Hydroxy Anisole, Butylated Hydroxy Toluene and the like from about 0.001% (w/w) to 5% (w/w), preferably 0.1% (w/w), more preferably 0.01% (w/w).

In a further embodiment of the present invention, the product of the preferred embodiment is further provided with a chelating selected from a group comprising Disodium EDTA and the like from about 0.01% (w/w) to 1% (w/w), preferably 0.5% (w/w), more preferably 0.1% (w/w).

In still another embodiment of the present invention, the product of the preferred embodiment is further provided with a humectant selected from a group comprising Glycerin, Sorbitol, Propylene glycol and the like from about 5% (w/w) to 40% (w/w) preferably 30% (w/w), more preferably 25% (w/w).

In another embodiment of the present invention, the product of the preferred embodiment further is provided with at least one component selected from a group comprising buffering agents, preservatives, anti oxidants, chelating agents, humectants, or any combination thereof in respective proportions disclosed in the earlier described embodiments.

In a further embodiment of the present invention, a novel dermaceutical cream is disclosed wherein sodium fusidate is converted in-situ under totally oxygen free environment by slow addition of an acid, into Fusidic acid of a molecular dispersion form (due to the presence of a co-solvent) at the intermediate stage, and which Fusidic acid regenerates into an extremely finely dispersed form when added to a final cream base, thereby resulting in a finely and homogeneously dispersed Fusidic acid in the final cream; all operations of converting sodium fusidate into Fusidic acid carried out preferably in an environment free of atmospheric oxygen.

Composition of the Typical Cream of the Preferred Embodiment of the Present Invention and on which the Experimental Results Presented in the Foregoing Description have been Based are Now Provided.

TABLE 27 i. Sodium Fusidate + Betamethasone Valerate Cream

| S. No | Ingredients | Specification | % (w/w) |
|---|---|---|---|
| 1 | Fusidic acid made from Sodium Fusidate | BP | 2.00 |
| 2 | Betamethasone Valerate | IP | 0.12 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 41.56 |

TABLE 28 ii. Sodium Fusidate + Fluticasone Propionate Cream

| S. No | Ingredients | Specification | % (w/w) |
|---|---|---|---|
| 1 | Fusidic acid made from Sodium Fusidate | BP | 2.00 |
| 2 | Fluticasone Propionate | BP | 0.05 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 41.6 |

TABLE 29 iii. Sodium Fusidate + Mometasone Furoate Cream

| S. No | Ingredients | Specification | % (w/w) |
|---|---|---|---|
| 1 | Fusidic acid made from Sodium Fusidate | BP | 2.00 |
| 2 | Mometasone Furoate | USP | 0.1 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 41.56 |

TABLE 30 iv. Sodium Fusidate + Dexamethasone Acetate Cream

| S. No | Ingredients | Specification | % (w/w) |
|---|---|---|---|
| 1 | Fusidic acid made from Sodium Fusidate | BP | 2.00 |
| 2 | Dexamethasone Acetate | BP | 0.1 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 41.56 |

TABLE 31 v. Sodium Fusidate + Hydrocortisone Acetate Cream

| S. No | Ingredients | Specification | % (w/w) |
|---|---|---|---|
| 1 | Fusidic acid made from Sodium Fusidate | BP | 2.00 |
| 2 | Hydrocortisone Acetate | IP | 1 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 40.65 |

TABLE 32 vi. Sodium Fusidate + Clobetasol Propionate Cream

| S. No | Ingredients | Specification | % (w/w) |
|---|---|---|---|
| 1 | Fusidic acid made from Sodium Fusidate | BP | 2.00 |
| 2 | Clobetasol Propionate | USP | 0.05 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 41.6 |

TABLE 33 vii. Sodium Fusidate + Beclomethasone Dipropionate Cream

| S. No | Ingredients | Specification | % (w/w) |
|---|---|---|---|
| 1 | Fusidic acid made from Sodium Fusidate | BP | 2.00 |
| 2 | Beclomethasone Dipropionate | IP | 0.025 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 41.6 |

TABLE 34 viii. Sodium Fusidate + Betamethasone Dipropionate Cream

| S. No | Ingredients | Specification | % (w/w) |
|---|---|---|---|
| 1 | Fusidic acid made from Sodium Fusidate | BP | 2.00 |
| 2 | Betamethasone Dipropionate | USP | 0.05 |
| 3 | Cetostearyl Alcohol | IP | 12.5 |
| 4 | White Soft Paraffin | IP | 12.5 |
| 5 | Polysorbate 80 | IP | 2 |
| 6 | Propylene Glycol | IP | 25 |
| 7 | Benzoic Acid | IP | 0.2 |
| 8 | Butylated Hydroxy Toluene | IP | 0.01 |
| 9 | Disodium Edetate | IP | 0.1 |
| 10 | 1M Nitric Acid | IP | 4.0 |
| 11 | Disodium hydrogen Orthophosphate anhydrous | IP | 0.05 |
| 12 | Purified Water | IP | 41.6 |

It is evident from the foregoing description that the present invention comprises the following embodiments.

1. A novel dermaceutical cream containing at least one corticosteroid, and Fusidic acid which is made in situ under oxygen-free environment using Sodium Fusidate, wherein said cream comprises Fusidic acid made in situ by a conversion of Sodium Fusidate, and a cream base containing at least one of each of a preservative, a primary and secondary emulsifier, a waxy material, a co-solvents, an acid, and water, preferably purified water.

2. A novel dermaceutical cream as described in item 1, wherein said corticosteroid is added from about 0.001% (w/w) to about 5% (w/w) by weight, preferably from about 0.005% (w/w) to about 2.00% (w/w) by weight, and most preferably from about 0.05% (w/w) to 1.0% (w/w) by weight and said Fusidic acid is present in an amount from about 0.1% (w/w) to about 25% (w/w), preferably from about 0.5% (w/w) to about 5% (w/w), and more preferably about 2.00% (w/w), and in which the amount of said Sodium Fusidate used to form in situ said Fusidic acid is in the range between about 0.1% (w/w) to about 25% (w/w), preferably from about 0.5% (w/w) to about 5% (w/w) and more preferably about 2.08% (w/w), and said preservatives is selected from a group comprising Methylparaben, Propylparaben, Chlorocresol, Potassium sorbate, Benzoic acid and the like, either singly or any combination thereof, to form a proportion from about 0.05% (w/w) to 0.5% (w/w), preferably 0.3% (w/w), more preferably 0.2% (w/w), said primary and secondary emulsifier is selected from a group comprising Cetostearyl alcohol, Cetomacrogol-1000, Polysorbate-80, Span-80 and the like, either singly or any combination thereof, to form a proportion from about 1% (w/w) to 15% (w/w), preferably 15% (w/w), more preferably 14.5% (w/w), said waxy material is selected from a group comprising White soft paraffin, Liquid Paraffin, Hard paraffin and the like, either singly or any combination thereof, to form a proportion from about 5% (w/w) to 20% (w/w), preferably 15% (w/w), more preferably 12.5% (w/w), said co-solvent is selected from a group comprising Propylene Glycol, Hexylene Glycol, PolyEthylene Glycol-400 and the like, either singly or any combination thereof, to form a proportion from about 5% (w/w) to 40% (w/w), preferably 30% (w/w), more preferably 25% (w/w), said acid is selected from a group comprising acids such as HCl, H2So4, HNO3, Lactic acid and the like, either singly or any combination thereof, to form a proportion from about 0.005% (w/w) to 0.5% (w/w), preferably 0.3% (w/w), more preferably 0.25% (w/w), and water in the amount in the range of 20% (w/w) to 75% (w/w), preferably 35% (w/w) to 50% (w/w), more preferably 40% (w/w) to 43% (w/w), preferably purified water.

3. A novel dermaceutical cream as described in item 1 which further comprises a buffering agent, wherein said buffering agent is selected from a group comprising Di Sodium Hydrogen Ortho Phosphate, Sodium Hydrogen Ortho Phosphate and the like, either singly or any combination thereof, to form a proportion from about 0.01% (w/w) to 1.00% (w/w), preferably 0.5% (w/w), more preferably 0.05% (w/w).

4. A novel dermaceutical cream as described in items 1 to 3 which further comprises an anti-oxidant, wherein said anti-oxidant is selected from a group comprising Butylated Hydroxy Anisole, Butylated Hydroxy Toluene and the like, either singly or any combination thereof, to form a proportion from about 0.001% (w/w) to 5% (w/w), preferably 0.1% (w/w), more preferably 0.01% (w/w).

5. A novel dermaceutical cream as described in items 1 to 4 which further comprises a chelating agent, wherein said chelating agent is selected from a group comprising Disodium EDTA and the like, either singly or any combination thereof, to form a proportion from about 0.01% (w/w) to 1% (w/w), preferably 0.5% (w/w), more preferably 0.1% (w/w).

6. A novel dermaceutical cream as described in items 1 to 5 which further comprises a humectant, wherein said humectant is selected from a group comprising Glycerin, Sorbitol, Propylene glycol and the like, either singly or any combination thereof, to form a proportion from about 5% (w/w) to 40% (w/w), preferably 30% (w/w), more preferably 25% (w/w).

7. A novel dermaceutical cream as described in items t to 6 wherein sodium fusidate is converted in-situ under totally oxygen free environment by slow addition of an acid, into Fusidic acid of a molecular dispersion form (due to the presence of a co-solvent) at the intermediate stage, and which Fusidic acid regenerates into an extremely finely dispersed form when added to a final cream base, thereby resulting in a finely and homogeneously dispersed Fusidic acid in the final cream; all operations of converting sodium fusidate into Fusidic acid carried out preferably in an environment free of atmospheric oxygen.

8. A novel dermaceutical cream as described in items 1 to 7 wherein said conversion of Sodium Fusidate into said Fusidic acid and the following formation of said Fusidic acid in a finely dispersed form in the final cream base take place in an oxygen-free environment.

9. A novel dermaceutical cream as described in item 8 wherein said oxygen-free environment comprises a gaseous environment formed of inert gas selected from a group comprising carbon dioxide, nitrogen, helium and the like.

10. A method of treating primary & secondary skin infections and inflammations said method comprising applying of a cream containing at least one corticosteroid and Fusidic acid which is made in situ under oxygen-free environment using Sodium Fusidate, wherein said cream comprises Fusidic acid made using Sodium Fusidate, a cream base containing a preservative, primary and secondary emulsifiers, waxy materials, co-solvents, acids, and water.

11. A method of treating primary & secondary skin infections and inflammations said method comprising applying of a cream as described in item 10, wherein said cream further comprises any of a group comprising a buffering agent, an anti oxidant, a chelating agent, and a humectant, or any combination thereof.

12. A method of treating primary & secondary skin infections and inflammations said method comprising applying of a cream as described in item 11, wherein said corticosteroid is added from about 0.001% (w/w) to about 5% (w/w) by weight, preferably from about 0.005% (w/w) to about 2.00% (w/w) by weight, and most preferably from about 0.05% (w/w) to 1.0% (w/w) by weight, said Fusidic acid is present in an amount from about 0.1% (w/w) to about 25% (w/w), preferably from about 0.5% (w/w) to about 5% (w/w), and more preferably about 2.00% (w/w), and in which the amount of Sodium Fusidate used to form in situ said Fusidic acid is in the range between about 0.1% (w/w) to about 25% (w/w), preferably from about 0.5% (w/w) to about 5% (w/w) and most preferably about 2.08% (w/w), said primary and secondary emulsifier is selected from a group comprising Cetostearyl alcohol, Cetomacrogol-1000, Polysorbate-80, Span-80 and the like, either singly or any combination thereof, to form a proportion from about 1% (w/w) to 15% (w/w), preferably 15% (w/w), more preferably 14.5% (w/w), said waxy material is selected from a group comprising white soft paraffin, liquid paraffin, Hard paraffin and the like, either singly or any combination thereof, to form a proportion from about 5% (w/w) to 20% (w/w), preferably 15% (w/w), more preferably 12.5% (w/w), said co-solvent is selected from a group comprising Propylene Glycol, Hexylene Glycol, PolyEthylene Glycol-400 and the like, either singly or any combination thereof, to form a proportion from about 5% (w/w) to 40% (w/w), preferably 30% (w/w), more preferably 25% (w/w), said acid is selected from a group comprising HCl, H2So4, HNO3, Lactic acid and the like, either singly or any combination thereof, to form a proportion from about 0.005% (w/w) to 0.5% (w/w), preferably 0.3% (w/w), more preferably 0.25% (w/w), said preservative is selected from a group comprising Methylparaben, Propylparaben, Chlorocresol, Potassium sorbate, Benzoic acid and the like, either singly or any combination thereof, to form a proportion from about 0.05% (w/w) to 0.5% (w/w), preferably 0.3% (w/w), more preferably 0.2% (w/w), said buffering agent is selected from a group comprising Di Sodium Hydrogen Ortho Phosphate, Sodium Hydrogen Ortho Phosphate and the like, either singly or any combination thereof, to form a proportion from about 0.01% (w/w) to 1.00% (w/w), preferably 0.5% (w/w), more preferably 0.05% (w/w), said anti-oxidant is selected from a group comprising Butylated Hydroxy Anisole, Butylated Hydroxy Toluene and the like, either singly or any combination thereof, to form a proportion from about 0.001% (w/w) to 5% (w/w), preferably 0.1% (w/w), more preferably 0.01% (w/w), said chelating agent is selected from a group comprising Disodium EDTA and the like, either singly or any combination thereof, to form a proportion from about 0.01% (w/w) to 1% (w/w), preferably 0.5% (w/w), more preferably 0.1% (w/w), and said humectant is selected from a group comprising Glycerin, Sorbitol, Propylene glycol and the like, either singly or any combination thereof, to form a proportion from about 5% (w/w) to 40% (w/w), preferably 30% (w/w), more preferably 25% (w/w), and said water in the amount in the range of 20% (w/w) to 75% (w/w), preferably 35% (w/w) to 50% (w/w), more preferably 40% (w/w) to 43% (w/w), preferably purified water.

It is evident from the foregoing description that the present invention has the following distinctions and advantages over the commercially available comparable products:

It has been prepared using Sodium Fusidate which is more stable than Fusidic acid It has a more stable and quality enriched Fusidic acid as the final API The Fusidic acid in the present invention degrades more slowly than the conventional products The stability level of the Fusidic acid in the present invention remains within the acceptable limits throughout the shelf life of the product The particle size of the Fusidic acid is finer and overall particle distribution in the cream is better, thereby providing better dermaceutical efficacy While the above description contains much specificity, these should not be construed as limitation in the scope of the invention, but rather as an exemplification of the preferred embodiments thereof. It must be realized that modifications and variations are possible based on the disclosure given above without departing from the spirit and scope of the invention. Accordingly, the scope of the invention should be determined not by the embodiments illustrated, but by the appended claims and their legal equivalents.

The invention claimed is:

1. A dermaceutical cream comprising:
(a) fusidic acid which is made in situ under an oxygen-free environment using sodium fusidate, wherein the cream comprises fusidic acid made by dissolving sodium fusidate in a co-solvent under inert gas purging and under vacuum, and converting the sodium fusidate to fusidic acid in situ by adding an acid under stirring;
(b) at least one corticosteroid; and
(c) a cream base comprising at least one preservative, at least one of each of primary and secondary emulsifier, a waxy material, and water.

2. The dermaceutical cream of claim 1, wherein:
the fusidic acid is present at a proportion from about 0.1% (w/w) to about 25% (w/w);
the corticosteroid is present at a proportion from about 0.001%(w/w) to about 5% (w/w);
the preservative is selected from the group consisting of methylparaben, propylparaben, chlorocresol, potassium sorbate, benzoic acid, and combinations thereof and is present at a proportion from about 0.05% (w/w) to 0.5% (w/w);
the primary and secondary emulsifier are selected from a group consisting of cetostearyl alcohol, cetomacrogol-1000, polysorbate-80, span-80, and combinations thereof and are present at a proportion from about 1% (w/w) to 15% (w/w);
the waxy material is selected from a group consisting of white soft paraffin, liquid paraffin, hard paraffin, and combinations thereof and is present at a proportion from about 5% (w/w) to 20% (w/w);
the co-solvent is selected from a group consisting of propylene glycol, hexylene glycol, polyethylene glycol-400, and combinations thereof and is present at a proportion from about 5% (w/w) to 40% (w/w);
the acid is selected from a group consisting of HCl, $H_2SO_4$, $HNO_3$, lactic acid, and combinations thereof and is present at a proportion from about 0.005% (w/w) to 0.5% (w/w); and
the water is present at a proportion from about 20% (w/w) to 75% (w/w).

3. The dermaceutical cream of claim 1, wherein the fusidic acid is present at a proportion from about 0.5% (w/w) to about 5.0% (w/w).

4. The dermaceutical cream of claim 1, wherein the corticosteroid is present at a proportion from about 0.05% (w/w) to about 1.0% (w/w).

5. The dermaceutical cream of claim 1, wherein the cream further comprises a buffering agent selected from the group consisting of disodium hydrogen orthophosphate, sodium hydrogen orthophosphate, and combinations thereof at a proportion from about 0.01% (w/w) to 1.00% (w/w).

6. The dermaceutical cream of claim 1, wherein the cream further comprises an anti-oxidant selected from the group consisting of butylated hydroxy anisole, butylated hydroxy toluene, and combinations thereof at a proportion from about 0.001% (w/w) to 5% (w/w).

7. The dermaceutical cream of claim 1, wherein the cream further comprises EDTA at a proportion from about 0.01% (w/w) to 1% (w/w).

8. The dermaceutical cream of claim 1, where in the cream further comprises a humectant selected from a group consisting of glycerin, sorbitol, propylene glycol, and combinations thereof at a proportion from about 5% (w/w) to 40% (w/w).

9. A method of treating primary and secondary bacterial skin infections and skin inflammations, the method comprising applying the cream of claim 1 to the skin.

10. A method of treating primary and secondary bacterial skin infections and skin inflammations, the method comprising applying the cream of claim 2 to the skin.

11. A method of treating primary and secondary bacterial skin infections and skin inflammations, the method comprising applying, the cream of claim 3 to the skin.

12. A method of treating primary and secondary bacterial skin infections and skin inflammations, the method comprising applying the cream of claim 4 to the skin.

13. A method of treating primary and secondary bacterial skin infections and skin inflammations, the method comprising applying the cream of claim 5 to the Skin.

14. A method of treating primary and secondary bacterial skin infections and skin inflammations, the method comprising applying the cream of claim 6 to the skin.

15. A method of treating primary and secondary bacterial skin infections and skin inflammations, the method comprising applying the cream of claim 7 to the skin.

16. A method of treating primary and secondary bacterial skin infections and skin inflammations, the method comprising applying, the cream of claim 8 to the skin.

* * * * *